US009901627B2

(12) United States Patent
Borodic

(10) Patent No.: US 9,901,627 B2
(45) Date of Patent: Feb. 27, 2018

(54) TOPICAL OCULAR PREPARATION OF BOTULINUM TOXIN FOR USE IN OCULAR SURFACE DISEASE

(71) Applicant: Revance Therapeutics, Inc., Newark, CA (US)

(72) Inventor: Gary E. Borodic, Quincy, MA (US)

(73) Assignee: Revance Therapeutics, Inc., Newark, CA (US)

( * ) Notice: Subject to any disclaimer, the term of this patent is extended or adjusted under 35 U.S.C. 154(b) by 0 days.

(21) Appl. No.: 14/803,574

(22) Filed: Jul. 20, 2015

(65) Prior Publication Data

US 2016/0015794 A1    Jan. 21, 2016

Related U.S. Application Data

(60) Provisional application No. 62/026,093, filed on Jul. 18, 2014.

(51) Int. Cl.

| | |
|---|---|
| *A61K 38/48* | (2006.01) |
| *A61K 45/06* | (2006.01) |
| *A61K 9/00* | (2006.01) |
| *A61K 31/245* | (2006.01) |
| *C12N 9/52* | (2006.01) |

(52) U.S. Cl.
CPC ........ *A61K 38/4893* (2013.01); *A61K 9/0048* (2013.01); *A61K 9/0051* (2013.01); *A61K 31/245* (2013.01); *A61K 45/06* (2013.01); *C12N 9/52* (2013.01); *C12Y 304/24069* (2013.01)

(58) Field of Classification Search
CPC ................................. A61K 38/4893
See application file for complete search history.

(56) References Cited

U.S. PATENT DOCUMENTS

| | | |
|---|---|---|
| 4,845,042 A | 7/1989 | Newman et al. |
| 4,861,627 A | 8/1989 | Mathiowitz et al. |
| 5,053,005 A | 10/1991 | Borodic |
| 5,069,936 A | 12/1991 | Yen et al. |
| 5,437,291 A | 8/1995 | Pasricha et al. |
| 5,512,547 A | 4/1996 | Johnson et al. |
| 5,562,906 A | 10/1996 | Amon |
| 5,562,907 A | 10/1996 | Amon |
| 5,576,468 A | 11/1996 | Lubowitz |
| 5,670,484 A | 9/1997 | Binder |
| 5,696,077 A | 12/1997 | Johnson et al. |
| 5,714,468 A | 2/1998 | Binder |
| 5,721,205 A | 2/1998 | Barnabas et al. |
| 5,756,468 A | 5/1998 | Johnson et al. |
| 5,766,176 A | 6/1998 | Duncan |
| 5,846,929 A | 12/1998 | Johnson et al. |
| 5,939,070 A | 8/1999 | Johnson et al. |
| 5,989,545 A | 11/1999 | Foster et al. |
| 6,051,239 A | 4/2000 | Simpson et al. |
| 6,087,327 A | 7/2000 | Pearce et al. |
| 6,100,306 A | 8/2000 | Li et al. |
| 6,203,794 B1 | 3/2001 | Dolly et al. |
| 6,210,707 B1 | 4/2001 | Papahadjopoulos et al. |
| 6,214,602 B1 | 4/2001 | Johnson et al. |
| 6,221,075 B1 | 4/2001 | Tormala et al. |
| 6,306,423 B1 | 10/2001 | Donovan et al. |
| 6,312,706 B1 | 11/2001 | Lai et al. |
| 6,312,708 B1 | 11/2001 | Donovan |
| 6,383,509 B1 | 5/2002 | Donovan et al. |
| 6,391,869 B1 * | 5/2002 | Parks .................. A61K 9/0031 514/211.07 |
| 6,429,189 B1 | 8/2002 | Borodic |
| 6,447,787 B1 | 9/2002 | Gassner et al. |
| 6,461,617 B1 | 10/2002 | Shone et al. |
| 6,545,126 B1 | 4/2003 | Johnson et al. |
| 6,573,241 B1 | 6/2003 | Bigalke et al. |
| 6,579,847 B1 | 6/2003 | Unger |
| 6,585,993 B2 | 7/2003 | Donovan et al. |
| 6,620,617 B2 | 9/2003 | Mathiowitz et al. |
| 6,622,051 B1 | 9/2003 | Bishay et al. |

(Continued)

FOREIGN PATENT DOCUMENTS

| | | |
|---|---|---|
| CA | 2376193 | 5/2000 |
| CH | 396311 | 7/1962 |

(Continued)

OTHER PUBLICATIONS

Whitemarsh et al., "Characterization of botulinum neurotoxin A subtypes 1 through 5 by investigation of activities in mice, in neuronal cell cultures, and in vitro," Infection and Immunity 81(10):3894-3902, Aug. 2013.*
Alster, "Review of lidocaine/tetracaine cream as a topical anesthetic for dermatologic laser procedures," Pain Ther 2:11-19, 2013.*
International Search Report and Written Opinion for PCT/US2011/036872 dated Sep. 14, 2011.
A Kohl, WH, et al. "Comparison of the effect of botulinum toxin A (Botox R) with the highly-purified neurotoxin (NT 201) in extensor digitorum brevis muscle test." Poster Sessions E & F, Wednesday, Jun. 14, 2000, p. 805.
Borodic, Gary et al. "Botulinum Toxin for Aberrant Facial Nerve Regeneration: Double-Blind, Placebo-Controlled Trial Using Subjective Endpoints." Facial Nerve Regeneration, vol. 116, No. 1:36-43, (Jul. 2005).

(Continued)

*Primary Examiner* — Rosanne Kosson
(74) *Attorney, Agent, or Firm* — Kenneth H. Sonnenfeld; Nicole Fortune; King & Spalding LLP

(57) ABSTRACT

A composition of botulinum toxin is claimed which can penetrate into the ocular surface inclusive of a penetration through a conjunctiva, cornea, and other structures. This composition allows for a maximal penetration of a topical preparation of botulinum toxin which serves to reduce the need for frequent allergy drops for the treatment of ocular surface disease and other conditions causing ocular surface inflammation or deep ocular inflammation. No puncture of the needle is necessary for the administration. Herein describes a novel composition using several principles based on composition, method of application, which enhances the effectiveness of the penetration.

31 Claims, No Drawings

(56) References Cited

U.S. PATENT DOCUMENTS

| | | | |
|---|---|---|---|
| 7,022,329 | B2 | 4/2006 | Donovan |
| 7,140,371 | B2 | 11/2006 | Zdanovsky |
| 7,192,596 | B2 | 3/2007 | Shone |
| 7,211,261 | B1 | 5/2007 | Moyer et al. |
| 7,220,422 | B2 | 5/2007 | First |
| 7,238,357 | B2 | 7/2007 | Barron |
| 7,270,826 | B2 | 9/2007 | Borodic |
| 7,288,529 | B2 | 10/2007 | Sanders et al. |
| 7,335,367 | B2 | 2/2008 | Borodic |
| 7,459,164 | B2 | 12/2008 | Borodic |
| 7,491,403 | B2 | 2/2009 | Borodic |
| 7,655,244 | B2 | 2/2010 | Blumenfeld |
| 7,691,394 | B2 | 4/2010 | Borodic |
| 7,943,152 | B2 | 5/2011 | Borodic |
| 7,964,199 | B1 | 6/2011 | Bigalke et al. |
| 8,192,979 | B2 | 6/2012 | Borodic et al. |
| 8,193,220 | B1 | 6/2012 | Scott |
| 8,241,640 | B2 | 8/2012 | Borodic |
| 8,398,998 | B2 | 3/2013 | Bigalke et al. |
| 8,580,745 | B2 | 11/2013 | Borodic |
| 8,679,486 | B2 | 3/2014 | Borodic |
| 9,066,851 | B2 | 6/2015 | Borodic |
| 2001/0043930 | A1 | 11/2001 | Aoki et al. |
| 2001/0053370 | A1 | 12/2001 | Donovan |
| 2002/0006905 | A1 | 1/2002 | Aoki et al. |
| 2002/0095158 | A1 | 7/2002 | Dixon et al. |
| 2002/0107199 | A1 | 8/2002 | Walker |
| 2002/0192239 | A1 | 12/2002 | Borodic et al. |
| 2002/0197279 | A1 | 12/2002 | Aoki et al. |
| 2003/0036502 | A1 | 2/2003 | Gassner et al. |
| 2003/0054975 | A1 | 3/2003 | Voet |
| 2003/0059912 | A1 | 3/2003 | Bigalke et al. |
| 2003/0086899 | A1 | 5/2003 | Jafari |
| 2003/0108597 | A1 | 6/2003 | Chancellor et al. |
| 2003/0113349 | A1 | 6/2003 | Coleman et al. |
| 2003/0118598 | A1 | 6/2003 | Hunt |
| 2003/0135241 | A1 | 7/2003 | Leonard et al. |
| 2003/0138437 | A1 | 7/2003 | Hunt |
| 2003/0143249 | A1 | 7/2003 | Lamb |
| 2003/0166238 | A1 | 9/2003 | Shone et al. |
| 2003/0180289 | A1 | 9/2003 | Foster et al. |
| 2004/0028703 | A1 | 2/2004 | Bigalke et al. |
| 2004/0037853 | A1 | 2/2004 | Borodic |
| 2004/0071735 | A1 | 4/2004 | Marchini et al. |
| 2004/0082540 | A1 | 4/2004 | Hermida Ochoa |
| 2004/0126396 | A1 | 7/2004 | Aoki et al. |
| 2004/0151741 | A1 | 8/2004 | Borodic |
| 2004/0170665 | A1 | 9/2004 | Donovan |
| 2004/0175400 | A1 | 9/2004 | Borodic |
| 2004/0247606 | A1 | 12/2004 | Borodic et al. |
| 2005/0031648 | A1 | 2/2005 | Brin et al. |
| 2005/0112146 | A1 | 5/2005 | Graham |
| 2005/0119694 | A1 | 6/2005 | Jacobs et al. |
| 2005/0142150 | A1 | 6/2005 | Graham |
| 2005/0208075 | A1 | 9/2005 | Borodic |
| 2005/0208076 | A1 | 9/2005 | Hunt |
| 2005/0214326 | A1 | 9/2005 | Hunt |
| 2005/0238663 | A1 | 10/2005 | Hunt |
| 2005/0238664 | A1 | 10/2005 | Hunt |
| 2005/0238667 | A1 | 10/2005 | Hunt |
| 2006/0147471 | A1 | 7/2006 | Borodic et al. |
| 2006/0269575 | A1 | 11/2006 | Hunt |
| 2007/0020294 | A1 | 1/2007 | Marchini et al. |
| 2007/0026019 | A1 | 2/2007 | Hunt |
| 2007/0129745 | A1 | 6/2007 | Suh et al. |
| 2007/0264373 | A1* | 11/2007 | Carroll .............. A61K 38/4893 424/780 |
| 2009/0232850 | A1 | 9/2009 | Manack et al. |
| 2009/0324647 | A1 | 12/2009 | Borodic |
| 2010/0028385 | A1* | 2/2010 | Nassif ................ A61K 38/4893 424/239.1 |
| 2010/0034853 | A1 | 2/2010 | Garcia et al. |
| 2010/0331259 | A1 | 12/2010 | Haunold et al. |
| 2011/0104061 | A1 | 5/2011 | Seward |
| 2011/0300245 | A1 | 12/2011 | Marshall |
| 2012/0088732 | A1 | 4/2012 | Bigalke et al. |
| 2012/0238504 | A1 | 9/2012 | Moyer et al. |
| 2014/0315820 | A1 | 10/2014 | Borodic |
| 2015/0157728 | A1 | 6/2015 | Modi |

FOREIGN PATENT DOCUMENTS

| | | |
|---|---|---|
| DE | 19856897 | 6/2000 |
| EP | 0593176 | 4/1994 |
| WO | 94/00481 | 1/1994 |
| WO | 96/39166 | 12/1996 |
| WO | 97/35604 | 10/1997 |
| WO | 99/03483 | 1/1999 |
| WO | 00/15245 | 3/2000 |
| WO | 00/24419 | 5/2000 |
| WO | 200139719 A1 | 12/2000 |
| WO | 01/58472 | 8/2001 |
| WO | 03/041724 | 5/2003 |
| WO | 04/060384 | 7/2004 |
| WO | 2009121632 A1 | 4/2009 |
| WO | 00174703 | 6/2009 |

OTHER PUBLICATIONS

Borodic et al. "Botulinum toxin therapy, immunologic resistance, and problems with available materials." Neurology 46:26-29, (Jan. 1996).

Johnson, H.M. et al. "The Use of a Water-Soluble Carbodiimide as a Coupling Reagent in the Passive Hemagglutination Test." The Journal of Immunology, vol. 97, No. 6: 791-796, (1966).

Pivalizza et al. "Avoidance of Epidural blood Patch in late Postpartum Eclampsia." J. Clin. Anesth., vol. 11 :615-616, (Nov. 1999).

Schmidt, J. J. et al. "Endoproteinase Activity of Type A Botulinum Neurotoxin, Substrate Requirements and Activation by Serum Albumin." Journal of Protein Chemistry, vol. 16(1 ):19-26, (1997).

Rollnik et al. "Low-Dose Treatment of Cervical Dystonia, Blepharospasm and Facial Hemispasm with Albumin-Diluted Botulinum Toxin Type A Under EMG Guidance." Eur Neural 2000; 43:9-12.

Goodnough et al. "Stabilization of Botulinum Toxin Type A during Lyophilization." Allied and Environmental Microbiology, Oct. 1992, p. 3426-3428.

Gassner et al. "Addition of an Anesthetic Agent to Enhance the Predictability of the Effects of Botulinum Toxin D Type A Injections: A Randomized Controlled Study." Mayo Clin Proc. Jul. 2000;75(7):701-4.

Epinephrine package insert #58-6165, Abbott Laboratories, pp. 1-5, May 2000.

Langhein et al. "Antibody response to bacterial antigens covalently bound to biodegradable polymerized serum albumin beads." Journal of Applied Bacteriology 1987, 63, 443-448.

International Search Report for PCT No. PCT/1803/06145 dated Aug. 11, 2005. All Pages.

International Search Report and Written Opinion for,PCT/US2006/ 015459 dated Mar. 1, 2007. All Pages.

Allergan, Inc. Botox® Product Insert, Revised Oct. 2004, 1-4, U.S.A.

Communication pursuant to Article 96(2) EPC for 03 814518.1-2107 dated Sep. 4, 2006.

Xeomin® product information, Merx Pharmacetuicals, LLC, pp. 1-17, see section 11, "Descrption", p. 8 for human serum albumin of 1 mg persent in the composition, and dated 2011.

Botox package insert Allergan Pharmaceuticals, pp. 1-4.

Borodic et al. "Botulinum B Toxin as an Alternative to Botulinum A Toxin, A Histologic study." Ophthalmic Plastic and Reconstructive Surgery 9(3): 182-190 (1993).

Troll et al. "Diplopia after cataract surgery using 4% lidocaine in the absence of Wydase (sodium hyaluronidase)." Journal of Clin Anesth. Nov. 1999; 11(7):615-6.

Borodic et al. "Botulinum A Toxin for Treatment of Aberrant Facial Nerve Regeneration." Plastic and Reconstructive Surger, (91)6: 1042-1045, 1993.

(56) References Cited

OTHER PUBLICATIONS

Schantz et al. "Standardized Assay for Clostridium Botulinum Toxins." Journal of the AOAC, vol. 61, No. 1, 1978.
Pearce et al. "The Median Paralysis Unit: A More Pharmacologically Relevant Unit of Biologic Activity for Botulinum Toxin." Toxicon, vol. 33, No. 2, pp. 217-227, 1995.
Wohlfarth et al., "Pharmacokinetic Properties of Different Formulations of Botulinum Neurotoxin Type A." Movement Disorders, vol. 19, Suppl. 8, 2004, pp. S65-S67.
Borodic. "Botulinum A Toxin for (expressionistic) ptosis overcorrection after frontal is sling." Ophtalmic Plastic & Reconstructive Surg. 8(2): 137-142, (1992).
Borodic et al. "Botulinum A Toxin for the treatment of spasmodic torticollis: Dysphagia and Regional Toxin Spread." Head & Neck, 12:392-398 (1990).
Nussgens et al. "Comparison of two botulinum-toxin preparations in the treatment of essential blepharospasm." Graefes Arch Clin Exp Ophtalmol 235(4): 197-199 (1997).
Bigalke et al. "Botulinum A Toxin: DYSPORT Improvement of biological availability." Exp. Neural. 168(1): 162-170 (2001).
Lew et al. "Botulinum toxin type B: a double-blind, placebo-controlled, safety and efficacy study in cervical dystoria." Neurology 49(3): 701-707 (1997).
Borodic et al. "Botulinum: a toxin for spasmodic torticollis, multiple vs single point injections per muscle." Head and Neck 14:33-37 (1992).
Ranoux et al. "Respective potencies of DYSPORT and BOTOX: a double blind, randomized, crossover study in cervical dystonia." J. Neuro. Neurosurg. Psychiatry 72:459-462 (2002).
Sesardic et al., "Role for standards in assays of botulinum toxins: international collaborative study of three preparations of botulinum type A toxin." Biologicals, vol. 31, 2003, pp. 265-276.
McLellan et al. "Therapeutic botulinum type A toxin: factors affecting potency." Toxion, col. 34(9), pp. 975-985, 1996.
Borodic et al., "New Concepts in Botulinum Toxin Therapy." Drug Safety 11(3): 145-152, 1994.
Marchetti et al., "Retrospective Evaluation of the Dose of Dysport and BOTX in the Management of Cervical Dystonia and Blepharospasm: The REAL DOSE Study." Movement Disorders, vol. 20, No. 8, 2005, pp. 937-944.
Giorgio et al. The Lancet, vol. 352, Aug. 22, 1998, pp. 6-25.
O'Day. "Use of botulinum toxin in neuro-ophthalmology." 2001, vol. 12(6), pp. 491-422.
Verheyden et al. "Other noncosmetic uses of BOTOX." Seminars in Cutaneous Medicine and Surgery, vol. 20(2), Jun. 2001, pp. 121-126.
Pearce et al. "Review Article: Pharmacologic Characterization of Botulinum Toxin for Basic Science and Medicine." Toxicon, vol. 35, No. 9, pp. 1373-1412, 1997.
Foote et al. "Albumin bound and alpha2-macroglobulin bound zinc concentrations in the sera of healthy adults." Journal of Clinical Pathology, vol. 37, Sep. 1984; 37(9):1050-4.
Masuoka et al. "Zinc (II) and Copper (II) Binding to Serum Albumin." The Journal of Biological Chemistry, vol. 269 (41) Oct. 14, pp. 25557-25561, 1994.
Carruthers et al, Skin Therapy Letter, vol. 13(6) Jul.-Aug. 2008, Botulinum toxin Products Overview, pp. 1-8.
Dressler et al, "Measuring the ptency labelling of onabotulinumtoxinA (Botox®) and incobotulinumtoxinA (Xeomin®) in an LD50 assay." J Neural Transm. 2012, vol. 119, pp. 13-15.

* cited by examiner

TOPICAL OCULAR PREPARATION OF BOTULINUM TOXIN FOR USE IN OCULAR SURFACE DISEASE

This non-provisional U.S. application claims priority to U.S. provisional patent application No. 62/026,093, filed Jul. 18, 2014, the disclosure of which is incorporated by reference herein in its entirety.

BACKGROUND OF THE INVENTION

Botulinum toxin is an agent proven useful in many clinical indications which involve suppression of motor nerve acetylcholine tip release from axon terminals which results in a flaccid paralysis. These applications have been used for the treatment of a wide variety of movement disease and diseases related to involuntary movement disorders such as dystonias. Additionally, the utility has also been spread to suppression of autonomic nervous system endings and the applications and reflex tearing of the eye, hyperhidrosis associated with aberrant facial nerve regeneration, Fabry's syndrome, and axial hyperhidrosis. These syndromes and additionally meibomian and sebum secretion have been known to be reduced with botulinum toxin injections. More recently injections of botulinum toxin have been found to be useful for treating ocular inflammation by inhibiting mass cell secretion and related conditions, and suppressing neurogenic inflammation by suppression of various neuropeptide such as substance P and CGRP and possibly histamine. Eczematous lesions around the eye have been successfully treated with botulinum toxin injections and such application has been found useful in a number of situations such as hypersecretion blepharitis. Animal models have been created to confirm the utility of this application using regional sensitization with artemis hydro folia (ragweed pollen). The suppressive effect of botulinum toxin injections in these situations to re-sensitization and re-exposure to a sensitized eye has been demonstrated in the laboratory.

A problem with periocular injections associated with the administration of botulinum toxin for allergic inflammation, as well as various forms of nonspecific inflammation, is the discomfort associated with the penetration of a needle through surface structure. Patients find this to be very threatening and find this to be very unacceptable in an approach to treating their disease. Eye drops are much more preferable and appealing to the patient. Herein describes a composition of botulinum toxin with anesthetic excipients designed and created to treat a patient suffering from ocular allergy, ocular surface disease, inflammation, uveitis, and various forms of vasospastic-related ocular disease.

BRIEF SUMMARY OF THE INVENTION

Most topical anesthetics including antihistamines, mass cell stabilizers, sympathomimetics, and nonsteroidal anti-inflammatories work by principles that are quite different than botulinum toxin. Virtually all of these methods require frequent dosing during the day and continued dosing. This is inconvenient to the patient and requires a thought process and time away from the daily schedule. Also, compliance issues occur when the dosing is frequent.

The utility of this new method of application, as well as the application of this new composition is that it will allow a long-term duration of one application of a topical drop the human eye, which would be quite preferable to all and any existing forms of therapy where frequent drops are needed. The reason for this long duration's intrinsic to the effective of botulinum toxin on human nervous and related structures, the cleavage of SNAP-25, which is the intercellular target for the light chain to the botulinum toxin, needs to be regenerated over a longer period of time. This also is a biochemical correlate to the effect on the human patient, which would benefit greatly from this long-acting pharmacology.

The composition involving a topical anesthetic permeation excipient with hypotonic or hypertonic formulation affords a solution to the inconvenience and need for daily dosing.

DETAILED DESCRIPTION OF THE INVENTION

In the preferred embodiment, the invention is a composition comprising topical application comprising a botulinum toxin; wherein the botulinum toxin is a topically-used, local anesthetic applied as a combined formulation to treat allergic conjunctivitis or various forms of ocular surface inflammation.

In another embodiment, the composition is a topical application is combined with a protein bulking agent. In a further embodiment, the protein bulking agent could be albumin or an albumin modification.

Tetracaine, lidocaine, Marcaine, and bupivacaine are topical anesthetics that have been used successfully in standard ophthamlmic practice and have an excellent safety record. In one embodiment, the topical application comprises a topical anesthetic selected from the group consisting of cocaine, bupivacaine, proparacaine, tetracaine, lidocaine, Xylocaine, novocaine, and piperocaine. Some of these compounds have strong bipoles in their molecular structure allowing them to, in fact, behave as penetrators through lipid membranes.

This is especially important for the mode of action, which involves penetration through a lipid membrane to the internal axon cylinder to interact with its receptor that is on the inner surface of the sensory nerve axonal membrane, the target for their mechanism of action. This observation indicates the importance of the lipid penetration of these bipolar molecules. The bipolar molecule and the topical anesthetic can be especially helpful in the application of the human eye. The topical anesthetic-botulinum toxin admixture botulinum toxin can penetrate through the bilipid layers into the eye effectively hitting the target's cellular organs, including sensory and autonomic nerves on the surface of the eye that can be active in reducing ocular surface inflammation associated with allergy and other conditions. The degree of penetration can also be enhanced by the use of an occlusion method. The occlusion method would be the closure of the eye, and the time of application of this new medicament. In one embodiment, the topical application is applied just prior to sleep, thus allowing enhanced contact time. The time of application would be most ideally used prior to sleep where a larger amount of viscous solution of tetracaine, lidocaine, Marcaine, bupivacaine, or cocaine or any one of a combination of these anesthetics to essentially affect a decrease in permeability. The closed eye will also act to keep the lidocaine in close penetration with the surface of the eye for a longer period of time.

Osmotic Shifts in Diurnal Variation in Osmolality of the Surface of the Eye

The ocular tear structure undergoes osmotic changes during the day. Generally speaking, the tear structure during sleep shows a lower osmolality. The lower osmolality of the tear film plays a functional role in the clarity of the human eye's cornea. The Descements membrane, the posterior membrane of the human cornea, functions as a water pump and sodium pump which keeps the cornea dehydrated and transparent. In the evening when there is no evaporation because of a closed eye the functionality of this pump as to by necessity, increase creating a relative osmotic flow across the cornea that is enhanced over daytime physiology. During the day the evaporation rate of the tears from the cornea is much higher as the exposure of surface area to open air allows for a higher evaporation rate and more concentrated tear structure. At night, however, the osmolality increases allowing for an increased flow of fluid into the cornea effectively creating an aqueous that is enhanced. This physiologic point can be used to further enhance the penetration of a combination of botulinum toxin, a bipolar topical anesthetic, and an application modality which would be inherent in increasing the effectiveness and of penetrating the ocular barrier with a painless form of botulinum toxin preparation.

Given these observations, the diurnal tear variation plays an important role of when to apply the botulinum toxin with the bipolar molecule. Application just prior to sleep has distinctly different properties relative to osmotic draw into deeper ocular surface layers further enhancing the bipolar effect of increased lipid and membrane permeability created by topical anesthetics.

Composition and Formulation

The composition and formulation will involve the topical anesthetic, as well as a type of botulinum toxin for the active pharmaceutical ingredient. In one embodiment, the botulinum toxin is any of the types A through G. In another embodiment, the composition comprises a botulinum toxin types selected from the group consisting of A sub-type 1, A sub-type 2, A sub-type 3, A sub-type 4, or A sub-type 5. These newer botulinum toxin sub-types have been recently identified in strains and various strains may have improved biologic activity over various other sub-types.

The teaching is that sub-type 1 or sub-type 2 will be the preferred strains.

In one embodiment, the composition comprises a botulinum toxin quantitated from 2.5 to 10 units per mL, from 10 to 25 units per mL, from 25 to 50 units per mL, from 50 to 75 units per mL, from 75 to 100 units per mL, from 100 to 125 units per mL, from 125 to 150 units per mL, from 150 to 175 units per mL, from 175 to 200 units per mL, from 200 to 225 units per mL, from 225 to 250 units per mL, from 250 to 275 units per mL, from 275 to 300 units per mL, from 300 to 325 units per mL, from 325 to 350 units per mL, from 350 to 375 units per mL, or from 375 to 400 units per mL.

In another embodiment, the botulinum toxin is quantitated using a neuronal cell-based assay that registers an equivalency against between 2.5 and 200 units per mL. In another embodiment, the botulinum toxin quantitated using a neuronal cell-based assay that registers an equivalency against from 2.5 and 400 units per mL. In another embodiment, the botulinum toxin quantitated using a neuronal cell-based assay that registers an equivalency against from 2.5 and 10 units per mL, from 10 and 25 units per mL, from 25 and 50 units per mL, from 50 and 75 units per mL, from 75 and 100 units per mL, from 100 and 125 units per mL, from 125 and 150 units per mL, from 150 and 175 units per mL, from 175 and 200 units per mL, from 200 and 225 units per mL, from 225 and 250 units per mL, from 250 and 275 units per mL, from 275 and 300 units per mL, from 300 and 325 units per mL, from 325 and 350 units per mL, from 350 and 375 units per mL, or from 375 and 400 units per mL.

The composition can involve an ointment, a solution, a liposomal-contained particle, or any form of possible fusion protein with botulinum toxin albumin or recombinant botulinum toxin as an active pharmaceutical ingredient.

In one embodiment, the composition is a combined formulation comprising a cohesive ointment. A cohesive ointment allows a longer contact time with the eye. In another embodiment, the ointment can be iso-osmotic, hypo-osmotic or hyperosmotic relative to the human corneal tissue and tear film.

In another embodiment, the composition is a solution.

Hyperosmotic solutions can essentially be used to further compromise the lipid barriers forming a higher degree of penetration. Hyperosmotic solutions can also create stress within the lipid membrane and to further enhance penetration. The use of polycationic proteins, such as protamine, can be used for further enhance penetrations with the anesthetic.

The focus, however, would be primarily an ointment applied that is relatively painless to the application and sustain an increased contact time. Increased contact time as previously mentioned can be enhanced by the use of scleral forms of contact lenses, closed eye over a period of time, or plugs within the nasolacrimal system. In one embodiment, the composition comprises a topical application that is applied with the placement of a contact lens. In another embodiment, the contact lens is a scleral contact lens.

Definition of Topical Anesthetic

Topical anesthetics usually can be divided into amino esters and imino amides. The following are typical for topical anesthetics for the purpose of this invention. Benzocaine, chloroprocaine, cocaine, Dimethocaine, larocaine, proparacaine, piperocaine, propoxycaine, novocaine, procaine, tetracaine, and amethocaine. These are either amino esters or imino amides. Generally, the imino amides are preferred because they are less allergic. It should be noted that each of these compounds do have some degree of lipid solubility, which is important in their effectiveness. It has also been postulated that use of lipid infusions can reverse toxicity due to these agents indicating the importance of binding capacity to lipids of these which are involved and integrated into the membrane barriers on the surface of the eye.

Treatment of Dry Eye Syndrome with a Topical Botulinum Preparation Containing a Topical Anesthetic for Enhancement of Epithelial Permeation:

A surprising finding with use of a topical botulinum toxin with permeation enhancement is the treatment of dry eye syndrome (see example 7 below). Note that botulinum toxin is a long acting anti cholinergic which should worsen dry eye syndrome by decreasing lacrimal secretion and secretion by assessory lacrimal glands in the ocular conjunctiva. In a counter intuitive observation, botulinum toxin with a topical anesthetic applied in one of two applications has been observed to decrease symptoms of eye irritation for an extended length of time well beyond the duration of action of the topical anesthetic. This effect is hypothesized to be the result of intrinsic changes to sensory nerves on the cornea resulting in alterations in cellular neurogenic tropic factors important to epithelial integrity and possible enhancement of ocular autonomic reflexes governing dry eye. Note to be limited by therapy, the medicine combination appeared to allow more comfort, less irritation and an increased dosing convenience resulting in an improvement of treatment option for this particular disease.

Enhancement Over Prior Methods

Most topical anesthetics including antihistamines, mass cell stabilizers, sympathomimetics, and nonsteroidal anti-inflammatories work by principles that are quite different than botulinum toxin. Virtually all of these methods require frequent dosing during the day and continued dosing. This is inconvenient to the patient and requires a thought process and time away from the daily schedule. Also, compliance issues occur when the dosing is frequent.

The utility of this new method of application, as well as the application of this new composition is that it will allow a long-term duration of one application of a topical drop the human eye, which would be quite preferable to all and any existing forms of therapy where frequent drops are needed. The reason for this long duration's intrinsic to the effective of botulinum toxin on human nervous and related structures, the cleavage of SNAP-25, which is the intercellular target for the light chain to the botulinum toxin needs to be regenerated over a longer period of time. This also is a biochemical correlate to the effect on the human patient, which would benefit greatly from this long-acting pharmacology.

Definition of Ocular Surface Inflammation and Allergy

Ocular surface inflammation can be secondary to atopic allergy, allergic blpeharitis, rosacea, dry eye syndrome, contact dermatosis, infections, allergic keratitis, drug allergy, seborrhea, staph infections, eczema, psoriasis, pemphagoid, herpes zoster infections, herpes simplex infections as well as any surface inflammation. Corneal ulcerations with respect to herpes simplex also indicated. In one embodiment, the composition is used to treat surface inflammation arising from herpes simplex or herpes zoster. In another embodiment, the composition is used to treat dry eye syndrome, intolerance to glaucoma medication, or acne rosacearelated ocular surface inflammation.

Each of these situations represents targeted indication as specific time during the disease cycles.

Duration of Applications:

The application may be applied at two week, one month, 6 week, 2 month 3 month intervals. The intervals are distinctly different in duration from all other forms of ocular medications making the formulation unique from a therapeutic perspective.

In one embodiment, the invention is a method of treating allergic conjunctivitis using composition comprising a botulinum toxin preparation and a topical anesthetic, wherein the composition is applied not more than once per month. In another embodiment, the invention is a method of treating allergic conjunctivitis using composition comprising a botulinum toxin preparation and a topical anesthetic, wherein the composition is applied, wherein the composition is applied once every season, about every 10 to 12 weeks.

Problems with the Treatment of Human Allergy with Corticosteroid Drops

Corticosteroid drops are very effective in treating allergic conjunctivitis and allergic problems with the human conjunctiva and also ocular surface disease and eye inflammation. They are noted to have side effects including the formation of cataracts and increase in intraocular pressure with steroid-induced glaucoma. The problem with the repeated use of steroids is that the side effects are substantial and could require the eye to be operated on or cause irreversible nerve damage to the optic nerve because of elevation of the intraocular pressure. Topical botulinum toxin has had no effect on intraocular pressure or optic nerve changes. Additionally there has been no history of cataract congenita from the injection of this periocular agent over the past 30 years. Given this new medicament, a selective advantage over existing therapies involves the use of anti-inflammatory drugs. Furthermore the long duration of action will necessarily enhance compliance.

The invention and composition described herein can be used independent or m conjunction with corticosteroid drops.

Concentrations of Local Topical Anesthetics

Although a number of topical anesthetics have been mentioned, this patent is not limited any single anesthetic which would be preferred. The most preferred is a bipolar anesthetic which has a rapid onset of action and causes the maximum penetration through the lipid barriers of the surface of the eye. This anesthetic would include any of the topical anesthetics mentioned at concentrations conventionally used for the human eye. These concentrations are readily available in the prior art, and the invention herein should not be limited by these concentrations, however, as higher concentrations are possible with greater degrees of penetration.

Rhinitis Associated with Allergic Conjunctivitis

Rhinitis is a condition that is commonly associated with allergic conjunctivitis. This involves sneezing, runny nose, and symptoms. Prior authors have previously described the effectiveness of botulinum toxin for rhinitis. Herein describes an invention that can also allow an enhanced treatment of human nasal mucosal inflammation from allergy by the natural flow of a teardrop through the nasolacrimal duct into the turbinates. When given during sleep this process would be slow and the application of the agent can take place in an immobilized head with less movement of air and less physical movement to allow maximum contact with nasal mucosa. This is a unique concept that the nasal disease can be treated with an eye drop of this nature. As it is a one-time application this could effectively work to reduce nasal symptoms and nasal discharge, as well as constant sneezing associated with human allergy.

Advantages of an Ocular Topical Formulation

Injections around the human eye in close proximity to conjunctiva, cornea and palpebral conjunctiva is potentially hazardous to inflicting paralysis of the extra-ocular muscles which results in diplopia. The topical preparations described herein allow for select delivery of the agents with enhanced penetration limited to the critical depths of the ocular surfaces to result in a beneficial effect on ocular surface disease. This concept is novel in the pharmacodynamic of drug delivery of a protein based composition. This notion allows for very high usages of botulinum toxin as measured by LD 50, nonograms, picogram, or any other measures of biologic activity.

Excipients and Bulking Agents:

Botulinum toxin therapeutic formulations including bulking agents which function to maintain stability and portability. Additionally, these bulking agent include proteins, which can be biologically active. Albumin which is the classic bulking agent has many >30% ions in the amino acid side chains. In recent times, the inventor has discovered the functional significance of albumin in formulations inclusive of increasing activity of the LD 50 unit, increasing nerve and axon uptake via increasing membrane permeability as well as stabilizing toxin. The result can be a higher potency and longer acting preparation. See, for example, U.S. patent application Ser. No. 14/225,011; U.S. Pat. No. 8,679,486; U.S. Pat. No. 7,691,394; U.S. Pat. No. 7,491,403; U.S. Pat. No. 7,459,164; and U.S. Pat. No. 8,580,745, all herein incorporated by reference in their entireties. The use of other protein stabilizer with cationic charges in the protein such as poly-lysine, protamine and others can be used.

pH is important and increased numbers of cations at lower pH's can be helpful. Other bulking agents include lipid complexed with proteins, hyaluronate with protein adjuvants, use of various lidocaine and related topical anesthetics as described here, and other forms of bipolar molecules. Additionally the human eye has the capability to have a contact lens placed on the eye which mechanically can abrade the surface causing increased penetration. The contact lens can be physically made out of a bulking agent, or complexed with a bulking agent to facilitate uptake through epithelial barriers and allow botulinum toxin to permeate through nerve and axonal membrane or membranes of other tissues important in ocular surface inflammatory diseases, including allergy, conjunctivitis, dry eye syndrome or other forms of ocular inflammatory diseases as described herein. An optimal formulation with pH between 5.6-7.4 would be preferred, with 6.4-7.0 being most optimal. It is of note that poly-lysine has been used to enhance antibiotics through membranes in the past and it is anticipated that albumin chimeric addition of increased amino acid polarity can be helpful in formatting a more functional bulking agent relative to botulinum penetration. The added peptides can be accomplished via recombinant or other technology. Additions or subtractions from the core albumin molecule could be accomplished to assist in perfecting this bulking agent towards permeation enhancement.

EXAMPLES

Example 1

The patient has bilateral severe atopic conjunctivitis requiring the use of intermittent steroids. The steroids caused an increase in intraocular pressure and steroids cause cataracts and also can be associated with increase in pressure and glaucoma. It was a medicament involving tetracaine, TetraVise, and botulinum toxin mixed at a unitage of about 50 units per mL. This medicament was applied to the eye, the eye was shut for a period of 90 minutes. The patient was then asked to return in 3 weeks. Only one eye was treated. Both eyes were equally symptomatic initially. When returned then she noticed substantial improvement in the treated eye in a single blinded patient fashion.

Example 2

The patient has had a history of severe atopic allergy, has had a history of intolerance to glaucoma medications because of sensitization to multiple medications. Botulinum toxin was added to TetraVise in a formulation that was about 50 units per 1 mL of TetraVise. This was applied to the eye. The patient was sent home to go to sleep and to take a nap. She slept for several hours. She noticed that the tolerance of the glaucoma drops to the eye treated was improved.

Example 3

The patient has had a history of chronic asthma and chronic atopic allergy. She notices that the eyes are constantly itching every spring. She has had a successful treatment with injections of periocular botulinum toxin for the treatment of human allergy and atopic blepharitis. She was treated with a topical TetraVise botulinum toxin preparation at a dose of about 50 units per 0.5 mL. She came back after 3 to 5 weeks and noticed that her symptoms have markedly diminished and the effect was continuing.

Example 4

The patient is given one application of a combination of TetraVise and 100 units of botulinum toxin per 0.5 mL. It is given prior to the allergy season. The patient comes back after 3 months of a one-time application for a repeat application allowing only 2 applications to the human eye per season.

Example 5

The patient has a history of low tension glaucoma, has had multiple obscurations of vision that seem to be associated with progression of a glaucomatous visual field defect. A medicament consisting of TetraVise and 100 units of botulinum toxin per mL is applied to the symptomatic eye. She notices improvement in the decrease in the frequency and duration of the obscurations of vision. Her pressure stays normal in the eye. She returns with no adverse effects to the human eye. No diplopia was noted.

Example 6

A patient suffering from dry eye syndrome is given one application of a combination of TetraVise and 100 units of botulinum toxin per 0.5 mL. It is given in conjunction or separate from other topic or systemic forms of treatment. The patient comes back after 3 months of a one-time application for a repeat application allowing only 2 applications to the human eye per season. Symptoms of irritation are mitigated. No diplopia was noted post treatment.

Example 7

A patient suffering from burning of associated with dry eye syndrome as diagnosed with Schirmer testing is treated with a combination of 20 U botulinum type A toxin mixed with tetracaine topical anesthetics. Relief in irritation burning and photophobia ensues for several weeks to several months. No diplopia was noted.

I claim:
1. A topical formulation comprising:
a botulinum toxin;
a topical anesthetic; and
a protein bulking agent.
2. The formulation of claim 1, wherein the topical anesthetic is selected from the group consisting of cocaine, bupivacaine, proparacaine, tetracaine, lidocaine, Xylocaine, novocaine, and piperocaine.
3. The formulation of claim 1, wherein the topical formulation is applied with the placement of a contact lens.
4. The formulation of claim 3, wherein the contact lens is a scleral contact lens.
5. The formulation of claim 1, wherein the topical formulation is a cohesive ointment.
6. The formulation of claim 1, wherein the formulation is a solution.
7. A topical formulation comprising:
a botulinum toxin; and
a topical anesthetic,
wherein the formulation is hypertonic relative to the human corneal tissue and tear film.
8. A topical formulation comprising:
a botulinum toxin; and
a topical anesthetic,
wherein the formulation is hypotonic relative to the human corneal tissue and tear film.
9. The formulation of claim 1, wherein botulinum toxin is type A.

10. The formulation of claim 9, wherein the botulinum toxin is selected from the types consisting of A sub-type 1, A sub-type 2, A sub-type 3, A sub-type 4, or A sub-type 5.

11. The formulation of claim 1, wherein the botulinum toxin is quantitated at 2.5 to 250 units per mL.

12. The formulation of claim 1, wherein the botulinum toxin is quantitated from 300 to 400 units per mL.

13. The formulation of claim 1 wherein the formulation is used to treat ocular surface inflammation arising from herpes simplex or herpes zoster.

14. The formulation of claim 1 in which the formulation is used to treat ocular surface inflammation related to dry eye syndrome, intolerance to glaucoma medication, or acne rosacea.

15. A method of treating allergic conjunctivitis comprising:
    selecting a patient having allergic conjunctivitis;
    applying a pharmaceutically effective amount of the formulation of claim 1 to the patient;
    thereby treating the allergic conjunctivitis.

16. The method of claim 15, wherein each application of the formulation effectively treats the allergic conjunctivitis for at least one month.

17. The formulation of claim 7, wherein the topical anesthetic is selected from the group consisting of cocaine, bupivacaine, proparacaine, tetracaine, lidocaine, Xylocaine, novocaine, and piperocaine.

18. The formulation of claim 7, wherein the topical formulation is a cohesive ointment.

19. The formulation of claim 7, wherein the formulation is a solution.

20. The formulation of claim 7, wherein botulinum toxin is type A.

21. The formulation of claim 7, wherein the botulinum toxin is quantitated at 2.5 to 250 units per mL.

22. The formulation of claim 8, wherein the topical anesthetic is selected from the group consisting of cocaine, bupivacaine, proparacaine, tetracaine, lidocaine, Xylocaine, novocaine, and piperocaine.

23. The formulation of claim 8, wherein the topical formulation is a cohesive ointment.

24. The formulation of claim 8, wherein the formulation is a solution.

25. The formulation of claim 8, wherein botulinum toxin is type A.

26. The formulation of claim 8, wherein the botulinum toxin is quantitated at 2.5 to 250 units per mL.

27. A topical formulation comprising:
    a botulinum toxin;
    a topical anesthetic, wherein the topical anesthetic is tetracaine.

28. The formulation of claim 27, wherein the topical formulation is a cohesive ointment.

29. The formulation of claim 27, wherein the formulation is a solution.

30. The formulation of claim 27, wherein botulinum toxin is type A.

31. The formulation of claim 27, wherein the botulinum toxin is quantitated at 2.5 to 250 units per mL.

* * * * *